United States Patent [19]

Blackmer et al.

[11] Patent Number: 4,773,410

[45] Date of Patent: Sep. 27, 1988

[54] METHOD AND APPARATUS FOR THE TREATMENT OF THE RESPIRATORY TRACK WITH VAPOR-PHASE WATER

[75] Inventors: Richard H. Blackmer; Christopher C. Consaul, both of Scotia, N.Y.

[73] Assignee: Transpirator Technologies, Inc., Somerset, N.J.

[21] Appl. No.: 70,142

[22] Filed: Jun. 25, 1987

Related U.S. Application Data

[63] Continuation of Ser. No. 659,405, Oct. 9, 1984, abandoned.

[51] Int. Cl.[4] .............................................. A61M 16/00
[52] U.S. Cl. ........................... 128/203.26; 128/203.27; 128/204.17; 128/207.18; 128/204.13
[58] Field of Search .................... 128/200.24, 203.12, 128/203.26, 203.27, 203.16, 203.17, 204.17, 207.18, 204.13

[56] References Cited

U.S. PATENT DOCUMENTS

| 2,868,199 | 1/1959 | Hudson | 128/207.18 |
|---|---|---|---|
| 3,972,321 | 8/1976 | Proctor | 128/207.18 |
| 4,060,576 | 11/1977 | Grant | 128/203.27 |
| 4,146,597 | 3/1979 | Eckstein et al. | 128/204.13 |
| 4,155,961 | 5/1979 | Behthin | 128/204.13 |
| 4,201,204 | 5/1980 | Rinne et al. | 128/203.27 |
| 4,355,636 | 10/1982 | Oetjen et al. | 128/204.17 |
| 4,369,777 | 1/1983 | Lwoff et al. | 128/204.17 |
| 4,381,267 | 4/1983 | Jackson | 128/204.13 |
| 4,401,114 | 8/1983 | Lwoff et al. | 128/204.17 |

Primary Examiner—Edward M. Coven
Assistant Examiner—K. M. Reiche
Attorney, Agent, or Firm—Kane, Dalsimer, Sullivan, Kurucz, Levy, Eisele and Richard

[57] ABSTRACT

A method and an apparatus are described which are useful for respiratory tract therapy. The method comprises contact of mucous membranes with vapor-phase water in the substantial absence of nucleating water-vapor condensation particulate, and includes the use of a heated delivery tube, unheated nasal cannula, for the delivery of a nasal cannula vapor/gas stream to a nasal passageway at delivery rates in excess of 8 liters per minute at dew point temperatures equal to or less than dry bulb temperatures and heating of a delivery tube vapor-gas stream to a temperature sufficiently greater than the canula nare dew point use temperature in order to cause a readily observable cannula condensation film to form near the exit use ports thereby signaling that the appropriate cannula delivery stream dew point-dry bulb temperature differential exists which insures that the dry bulb nare exit temperature is equal to or greater than the nare dew point use temperature.

2 Claims, 5 Drawing Sheets

METHOD AND APPARATUS FOR THE TREATMENT OF THE RESPIRATORY TRACK WITH VAPOR-PHASE WATER

This application is a continuation of application Ser. No. 659,405, filed Oct. 9, 1984, now abandoned.

A method and an apparatus are described which are useful for respiratory tract therapy which comprises contacting mucous membranes with vapor-phase water in the substantial absence of nucleating water-vapor condensation particulate.

The method comprises (a) the use of an unheated nasal cannula heated delivery tube in a respiratory tract and/or mucous membrane treatment with a vapor gas stream at nasal cannula vapor/gas delivery rates in excess of 8 liters per minute at dew point temperatures equal to or greater than dry bulb temperatures and (b) heating the delivery tube vapor/gas stream to a temperature sufficiently greater than the cannula nare dew point use temperature whereby a readily observable cannula condensation film indicates that a cannula delivery stream dew point dry bulb temperature differential exists and that the dry bulb nare exit temperature is equal or greater than the nare dew point use temperature.

TECHNICAL BACKGROUND

Various devices have been patented which are useful in respiratory therapy as well as hyperthermic treatment of nasal respiratory tract. The benefits associated with the use of these devices include the treatment of the common cold, allgeric rhinitis, emphysema, etc. These devices are designed to provide gas streams enhanced in either air, oxygen and/or water/water-vapor at temperatures ranging from ambient room to 44 degrees Centigrade (approx. 112 degrees Fahrenheit) or higher to respiratory and/or nasal respiratory tract at atmospheric or higher pressures. Each device uses different design parameters for regulating air/vapor-gas stream temperature, water/water-vapor and/or air, oxygen content at fixed gas stream flow rates.

Illustrative descriptions of these devices are set out in U.S. Pat. No. 4,369,777 Issued 1/25/83 and U.S. Pat. No. 4,401,114 Issued 9/30/83 both assigned to Yeda Research and Development Company, LTD. Although the above mentioned devices are useful in respiratory and respiratory tract support and/or treatment their commercial, economic and therapeutic efficacy is sometimes limited due to inherent cooperating limitations, such as: (a) water and/or water containers must be sterilized prior to use, (b) air stream/water-vapor transfer locations are susceptible to liquid condensation/collection which facilitates bacteria growth, thus requiring disposal, repurchase, and replacement of significant portions of the device after each use, and (c) non-uniform inhomogeneous wet gas—containing widely varying amounts of liquid and air having widely varying at different temperatures e.g. $H_2O(112F/44.4C)$ vs air (135F/57.2C)—is delivered to respiratory or respiratory tract tissue causing significant patient discomfort.

DESCRIPTION OF THE INVENTION

The invention described herein comprises an apparatus that provides a sterile condensate-free water-vapor/gas stream having a substantially uniform dew point/dry bulb temperature and a nasal cannula method of treating respiratory tract with a substantially sterile condensate free water-vapor/gas stream having a substantially uniform dew point/dry bulb temperature.

The method also includes (a) the use of an unheated nasal cannula heated delivery tube in a respiratory tract and/or mucous membrane treatment with a vapor gas stream at nasal cannula vapor/gas delivery rates in excess of 8 liters per minute at dew point temperatures equal to or greater than dry bulb temperatures and (b) heating the delivery tube vapor/gas stream to a temperature sufficiently greater than the cannula nare dew point use temperature whereby a readily observable cannula condensation film indicates that a cannula delivery stream dew point dry bulb temperature differential exists and that the dry bulb nare exit temperature is equal or greater than the nare dew point use temperature.

Broadly, the apparatus comprises the following operatively coupled components (A) a permeable membrane structured and adapted to permit a liquid-vapor boundary to form adjacent to an opposing vapor-gas boundary, (B) means for delivering a gas to a vapor-gas/liquid-vapor boundary, (C) means for delivering a liquid to a liquid-vapor membrane boundary substrate from a membrane location disposed and spaced apart from a vapor-gas membrane boundary, (D) means for delivering a vacuum to a liquid-vapor boundary, (E) means for delivering pressure to a vapor-gas membrane boundary, (F) means for delivering heat to a liquid-vapor membrane substrate, and (G) means for delivering a substantially condensate free saturated vapor-gas stream to a respiratory and/or another respiratory tract.

Benefits associated with the apparatus and the methods described herein vis-a-vis the TECHNICAL BACKGROUND referenced devices and/or therapeutic methods associated therewith follow:

(1) An aseptic vapor phase molecular water gas stream phase is maintained and/or transferred—under both static and dynamic operating conditions—to a respiratory and/or nasal respiratory tract gas stream. The delivery is readily monitored and controlled by individual/patient user and/or medical doctor/nurse/therapist, etc.;

(2) The heat transfer rate and the heat distribution from the saturated water-vapor/gas stream to respiratory tract is uniformly distributed and controlled as heat transfers from the saturated-water-vapor/gas stream to respiratory tract tissue;

(3) Controlled flow and temperatures of water-vapor/gas streams are delivered to nasal mucous and/or respiratory membranes in the absence of deleterious hydration/dehydration water-vapor-gas condensation-/evaporation latent heat tissue affects;

(4) Aseptic mixtures of gases including water-vapor, oxygen, air, anesthetics, drugs, etc. can be dispensed in a saturated water-vapor atmosphere; and, (5) Body temperatures through internal respiratory/circulatory systems can be regulated in the substantial absence of thermal shock.

BEST MODES FOR CARRYING OUT THE INVENTION

Figure 1:
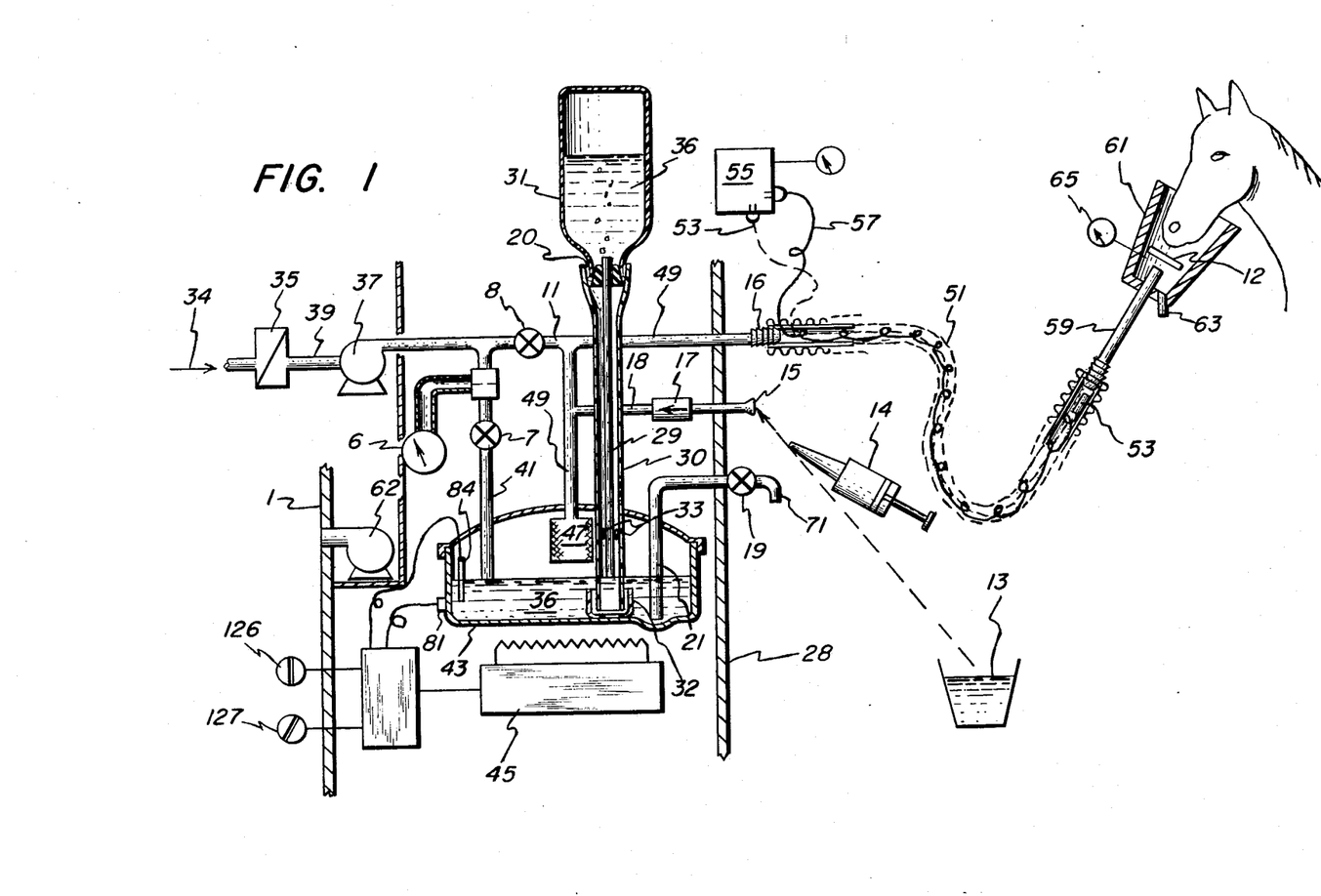
FIG. 1 is a schematic diagram of a presently preferred apparatus according to the invention.

Referring to FIG. 1, one of the presently preferred apparatuses of this invention is shown.

In operation air 12 enters frame 1 through external 90 and internal 92 air filters at atmospheric pressure. Sequentially, air under vacuum provided by gas compressor 15 passes into gas intake port 14; gas quality regulator 17, e.g., a bacteria filter; gas flow gauge 33, e.g., a gas flow meter; gas flow regulator 16, e.g., a manually operated air flow control valve; and compressor 15. Sequentially, air exits compressor 15 passing through gas quality regulator 18, e.g., another bacteria filter; gas pressure check valve 20; relief valve "T"35; gas dew point "T"36; optional auxiliary gas intake "T"37—connected to auxilary gas intake port 34; and gas inlet membrane cartridge port 3. Gas pressure relief valve 19 functions to limit/vent deleterious excess internal fiber (not shown) pressure. Gas dew point gauge 32 is connected upstream of inlet port 3 by conduit 138 at "T"36.

Still referring to FIG.1, liquid 10 is passed to liquid inlet port 5—positioned downstream of the gas flow direction within membrane container 2—under vacuum from sequestered container 21. Sequentially, liquid passes through a liquid flow chamber (not shown) within container 2 and permeates external fiber surfaces (not shown), e.g., hollow cellulous acetate hydrophilic fiber external surfaces, wherein an internal liquid-vapor boundary substrate is formed opposing an adjacent vapor-gas boundary. Liquid passes from outlet port 6 to liquid vacuum pump 23; liquid heater 24—regulated by a liquid temperature regulator 25 including thermal switch and thermistor 84; and returns to container 21. Suction pressure relief valve 22 positioned between liquid pump inlet and outlet "T's" 38 and 39 stablizes and maintains safe operating external liquid hollow fiber pressures, e.g., negative external fiber pressures of less than negative. 1 to 3 pounds per square inch. A liquid ambient room temperature reservoir 31 connected to sequestered liquid reservoir 21 replenishes water extracted from the sequestered container 21. Liquid temperature gauge 40 provides a visual means of determining if liquid within container 21 is above/equal/below desired saturated vapor-gas stream temperature exiting vapor/gas outlet port 4.

Still referring to FIG.1, membrane container 2 back pressure valve 29 regulates the resistance to flow of the water-vapor-gas outlet delivery to tube 26—containing vapor-gas outlet heater 28, and thereby regulates expansion of the gas passing to delivery tube 26 and nasal cannula 51. Output heater control 41 represents collectively various vapor-gas delivery control systems including heated delivery tube transformer, fixed resistor, electronic light switch, and power lights elements (all not shown) that are interactive with heating elements 28 and 30, heated delivery tube connector 54 and thermal switch 43. Valve 29 regulates the high humidity gas flow within the cannula and thus controls the location of any surface (non-particulate) condensation within the cannula 51. During use the gas flow is preferentially adjusted so that condensation occurs in very close proximity (⅛ inch downstream) of vapor gas exit use ports 27. Cannula 51 is a disposable apparatus portion which may physical contact a portion of a nasal respiratory track. The function of valve 29 is to provide a positive gas back pressure thereby (a) limiting vapor condensation within delivery tube 26/cannula 51 to de minimus amounts and
(b) preventing liquid penetration of the internal membrane (inside diameter) fiber surface of the cannula 51 under both static and dynamic operating conditions.

Combination of air with other gases such as supplemental oxygen, anesthetics, and/or drugs in vapor form can be readily carried out by introduction supplemental at intake port 34 at suitable operating temperatures/pressures.

Figure 2:
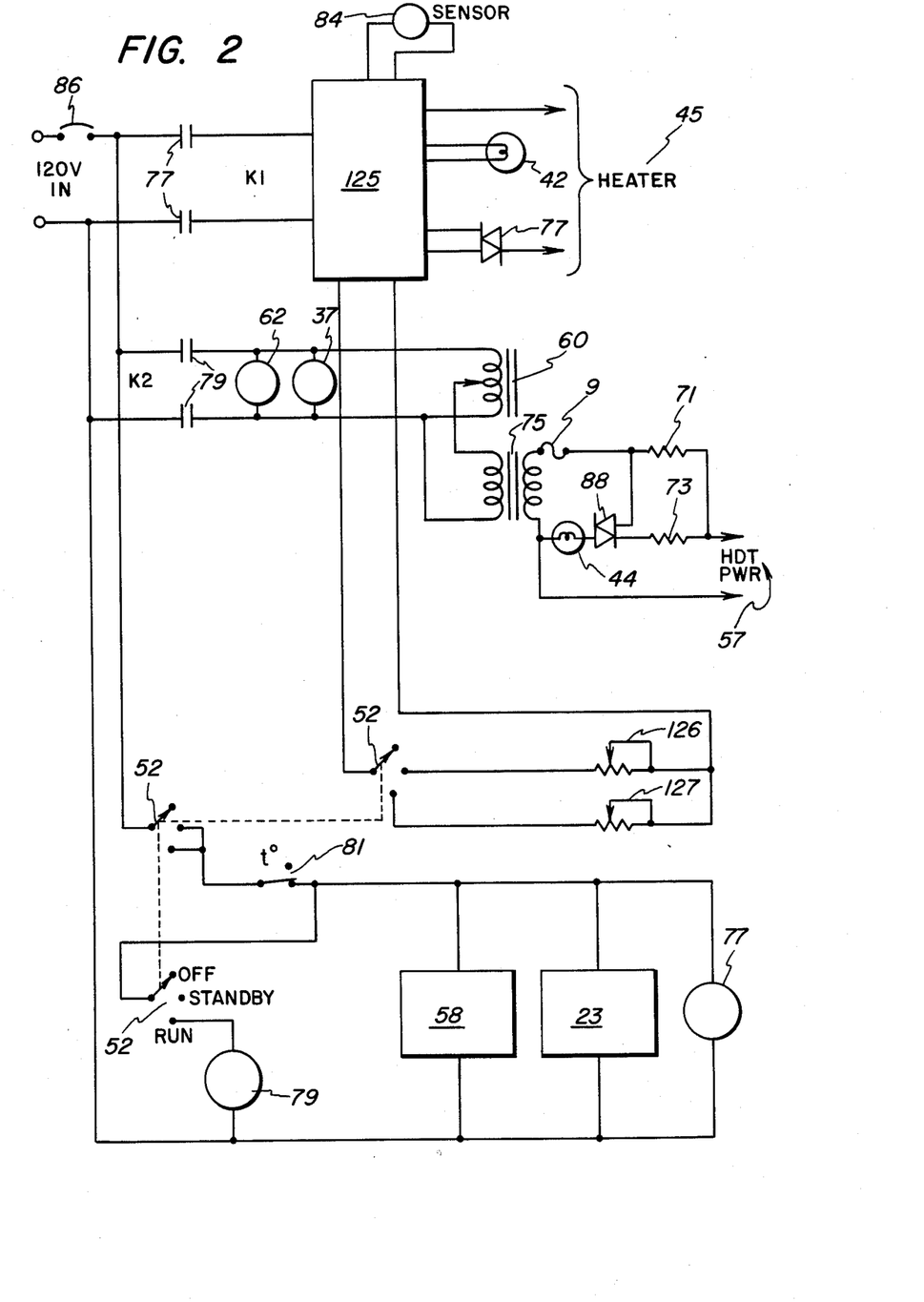
FIG. 2 is a schematic electric control circuit diagram of a FIG. 1 apparatus.

Referring to FIG. 2, the electrical system includes optionally two or three wire power cord 63 connected through five position power selector switch 52; circuit breaker 86; relays 66 and 68; MOV transient suppressor 77; gas compressor 15; compressor starter capacitor 69; liquid vacuum pump 23; power timing meter 58; temperature control printed circuit (PC) board 125; liquid cartridge heater 24; liquid heater power light 42; overtemp thermostat and thermistor 84; Vapotherm TM (respiratory therapy unit) elapsed total time indicator 59; variable current transformer 60; heated delivery tube transformer 75 which regulates power to heating elements 28 and 30, thermal switch 43, connector 54, fixed resistors 71 and 73, power light 44 and electronic light switch 88. Heating element 28 and thermal switch 43 are connected to heated delivery tube connector 54. Also connected to switch 52 are overtemp fault light 45; audio alarm 46; relay 70; air circulation fan 62; multipole relay 72 controlling switches 66, 68, 70, and 74; Vapotherm TM timer/switch 59; multi-pole relay 76 controlling switches 78, 80 and 82; hyperthermia light 55 and audio alarm 56 activity indicators. Thermoswitches 64 and 65 act in conjunction with relay switches 80 and 82 including fixed position resistor 126 (trimmers 1, 2 and 3) and control printed circuit board 125 power input.

Figure 3:
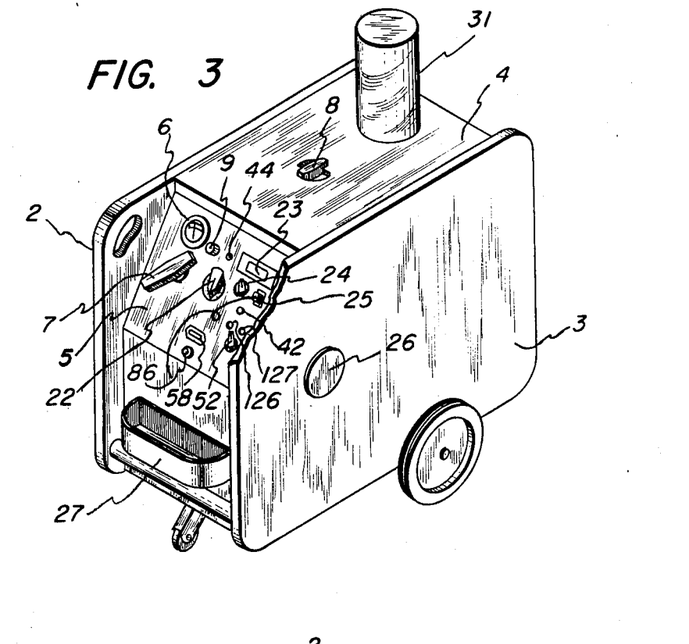
FIG. 3 is a front perspective view of a FIG. 1 apparatus with the outside frame in place.

Referring now to FIG. 3, a front perspective view is shown which includes frame 1; membrane container 2; vapor/gas outlet port 4; liquid inlet and outlet ports 5 and 6; membrane header heater housing 103; membrane support saddle 104 mounted on membrane chamber basin 106; auxilary gas intake port 34; optional auxilary gas intake "T"37; back pressure valve 29; inlet gas flow inlet regulator 16; sequestered liquid container 21; liquid room temperature reservoir 31; gas flow gauge 33; dew point gauge 32; liquid heater power light 42; vapor/gas delivery tube power light 44; vapor/gas delivery tube overtemp light 45; liquid container outlet 48 conduit; liquid container inlet return 50; power selector switch 52; heated delivery tube connector 54; Vapotherm TM hyperthermia light 55 and Vapotherm TM hyperthermia elapsed time indicator 59; vapor/gas delivery tube temperature regulator 60; external air filter 90; and control panel 98.

Figure 4:
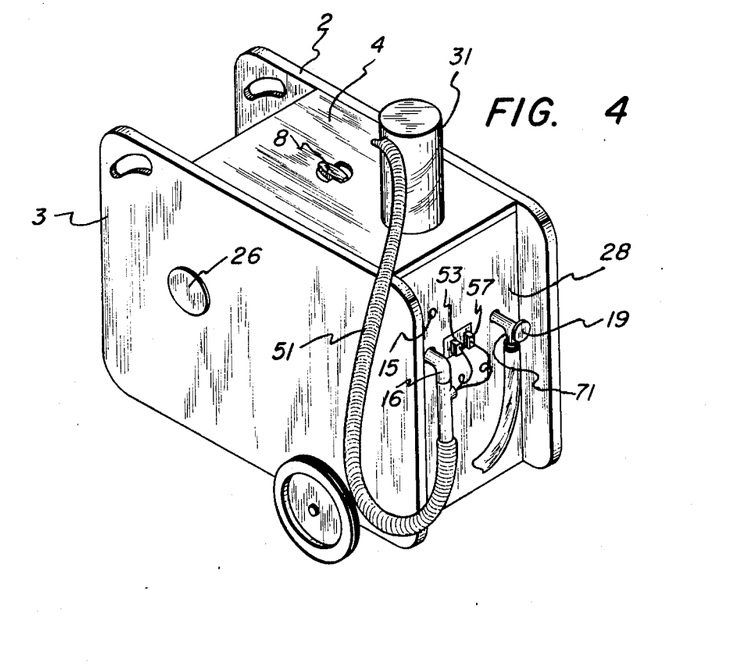
FIG. 4 is a right rear oblique interior view of the FIG. 3 apparatus with the outside frame removed.

As shown in FIG. 4, the apparatus has a front core panel 96 in which a control panel 98 is mounted. Membrane container 2 containing gas inlet port 3; liquid inlet and outlet ports 5 and 6 coupled with back pressure valve 29; auxilary gas intake port 34; optional auxilary gas intake "T"37; is supported by membrane header heater housing 103 and membrane support saddle 104. Both housing 103 and saddle 104 are mounted on membrane chamber basin 106 containing liquid outlet conduit port (not shown). Connected to basin outlet port is conduit 110 which extends to outlet port 112 located in core floor 116. Housing 103 suppports header heater electric resistance wire (not shown). Mid-core 114 meets the top surface of bottom core panel 116 and extends from the rear edge of panel 116 to the front edge of panel 96. A rectangular slot 117 is located in vertical panel 114. In operation air 12 enters core cabinet inlet duct and passes through filters 90 and 92 to gas intake port 14; bacteria filter 17; and to gas flow meter (not shown). Gas flow regulator valve 16; lights 42, 44, and 45 (all partially shown) pass through panel 98. Vertical mid-core 114 extends to the top rear and bottom edges (both not shown) of the core ceiling panel 120 and the rear surface of front control panel 98.

Further referring to FIG. 4, liquid inlet conduit 48 after passing through panel 98 and is supported by panel 114. Conduit 48 passes through (not shown) basin 106 and is connected to membrane container 2 at port 5. Liquid containment return conduit 50 exits from the bottom of basin 106; and passes in a downwardly direction supported by mid-core panel 114 to inlet "T" 38, and to liquid vacuum pump 23. In operation liquid passes through vacuum pump outlet conduit 124 upwardly through "T" 39 to the top of liquid heater core 24 operatively coupled with thermister 84 and thermoswitches 64 and 65. Liquid passes from the bottom of heater core 24 upwardly through conduct 50 and panel 98 to sequestered container (not shown).

Figure 5:
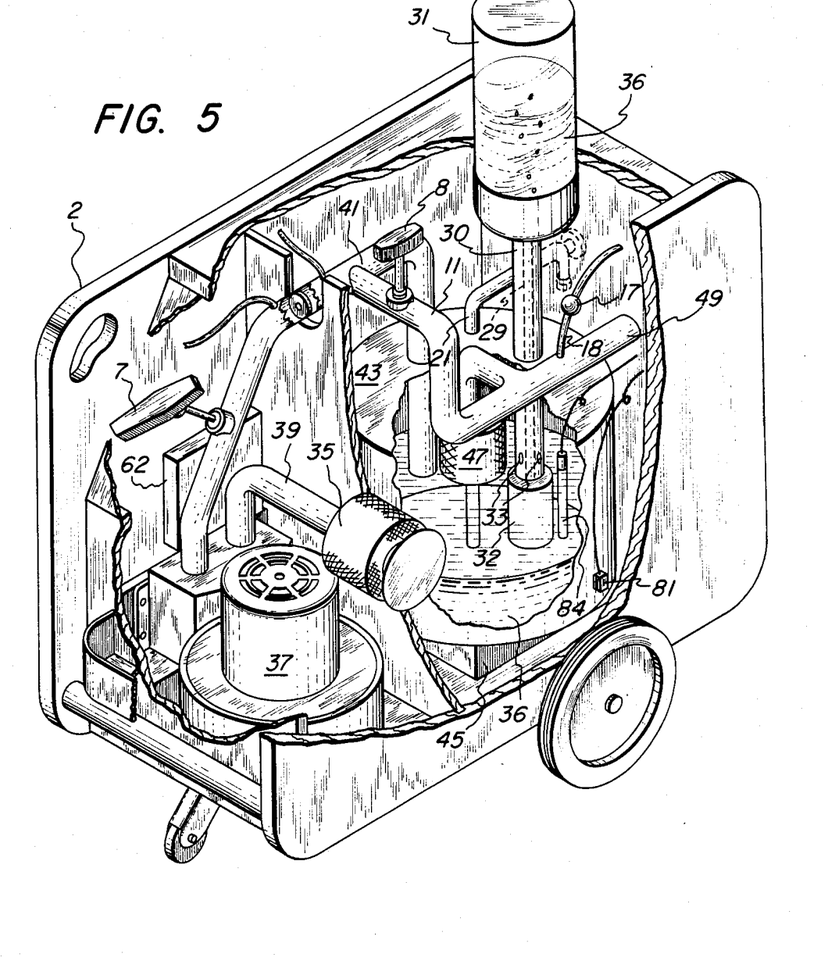
FIG. 5 is a left rear oblique interior view of the FIG. 3 apparatus with the outside frame removed.

Referring now to FIG. 5 mounted and passing through panel 98 are variable current transformer 60; Vapotherm TM light 55; Vapotherm TM timer switch 59; heated delivery tube connector 54; dew point gauge 32; and power switch 52. Mounted on mid-core panel 114 are audio signals 46 and 56; PC board 125; fixed resistance 126 (trimmers 1, 2, 3); fixed resistors 71; electronic light switch 88; and multi-pole relay 76 controlling relay switches 80 and 82 (not shown).

Further as illustrated by FIG. 5 horizontal core panel 134 meets the left side of panel 114 and extends from control panel 98 to near the rear edge of mid-core panel 114. Mounted on panel 134 are MOV transient suppressor 77; multi-pole relay 72 controlling relay switches 66, 68, 70, and 74 (not shown); fan 62; circuit breaker 86 positioned on the top of power timing meter 58; liquid pump fuse (not shown); and variable transformer fuse (not shown) and compressor starter capacitor 69 (mounted below panel 134). A two headed single stage positive pressure pump 15 connected to gas inlet 47 and gas outlet 49 is supported on the core floor 116.

Referring to FIGS. 4 and 5, in operation gas inlet conduit 47 connected to valve 16 passes in a downwardly direction to and through mid-core panel 114, to the inlet ports of the two-headed single stage positive compressor pump 15. Gas conduit 49 exits pressure pump 15 at exits ports (not shown) and passes upward, sequentially, to bacteria filter (not shown); and through a rear vertical core panel 136—which extends up from panel 116 co-extensive with mid-core panel 114 to panel 134. Conduit 49 passes, sequentially, downwardly and connects check valve 20—supported by panel 136, "T" 35, relief valve 19, "T"36—which is connected to dew point gauge conduit 138, passes through mid-core panel 114 and membrane basin 106; and connects "T" 37—connected to auxilary port 34 with membrane gas inlet port 3. Membrane container 2 inlet port 3; liquid inlet and outlet ports 5 and 6 as well as back pressure valve 29 function as described hereinbefore.

Figure 6:
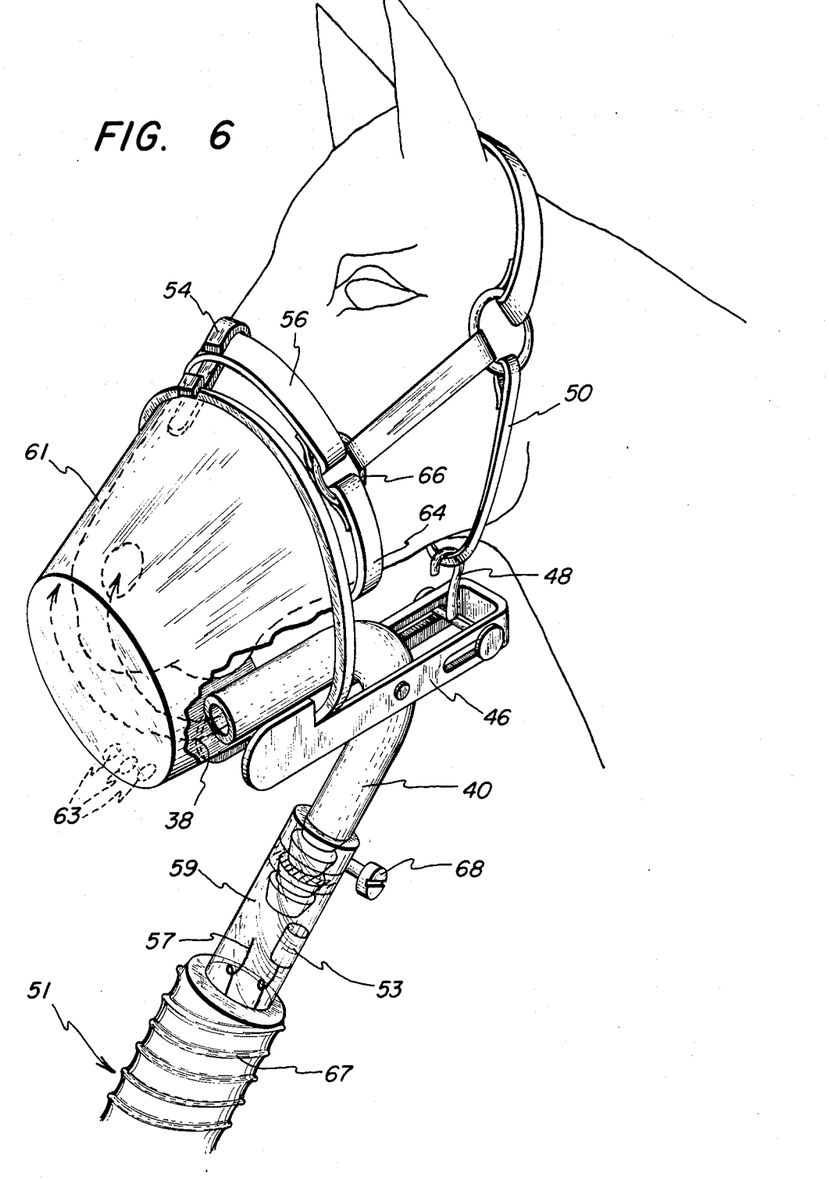
FIG. 6 is an internal sectional partial view of membrane permeable fibers of a membrane container.

Referring to FIGS. 1 & 6, an internal partial cross-section of a fiber bundle contained within a commercial membrane cartridge 2, is illustrated. Commercial hollow fiber dialyzers containing hollow (permeable membrane) fibers are marketed by TERUMO Corporation and contain CUPROPHAN TM hollow fibers membranes manufactured by ENKA A.G. The hollow fibers 11 having internal surface 13(not shown) are, commonly, 300 or 200 microns in diameter with 16 or 11 micron thick walls, respectively. The detailed construction of hollow fiber cartridge membranes is well known to those of ordinary skill in the art and accordingly are not described herein indepth. Any permeable hollow fiber membrane cartridge that can be employed in the operation of artifical kidneys for dialyzes purposes can also be employed in the apparatuses's of this invention—subject to well known bubble point limitations. The composition of the membrane fibers can be hydrophobic or hydrophilic hollow fiber materials, e.g., cellulose acetates, polyvinylchlorides, polyacrylonitrilles, polycarbonates, polysulfones, polyamides, polyetherimides, polyimides, etc. Typical hollow-fiber membranes have thin surface skin supported by a porous sub-structure. Preferrably employed in the operation of the apparatus of this invention are the well known hydrophilic cellulose acetate hollow-fibers.

For the purposes of brevity relative to fiber membrane technology incorporated herein by reference in its entirety—including articles referenced therein is the publication entitled "Membrane Separation Processes", authored by Lynn E. Applegate, Chemical Engineering, (June 11, 1984), Pages 64–89, including the referenced U.S. Pat. Nos. 3,567,632; 3,951,815; and 4,278,548.

Figure 7:
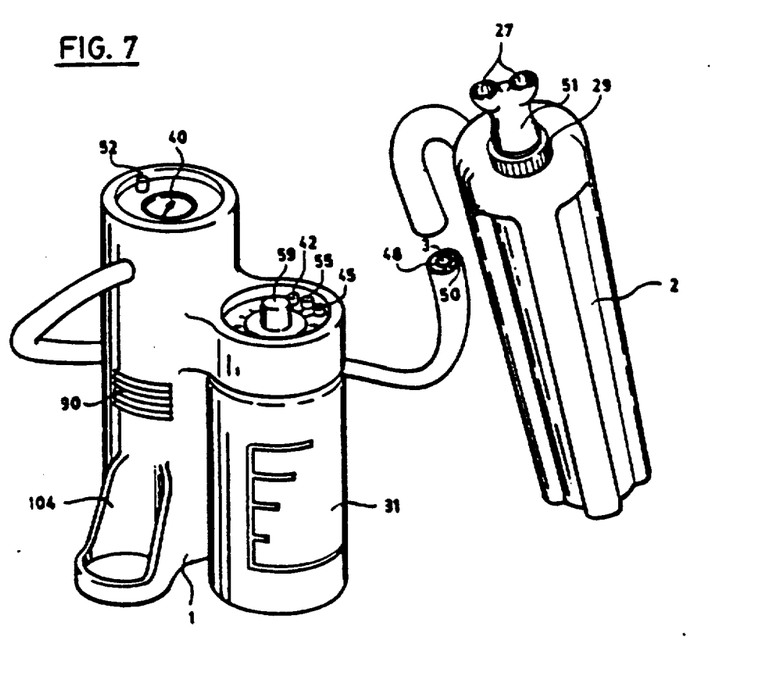
FIG. 7 is a design of an apparatus according to the invention.

Referring now to FIG. 7. a design embodiment of this invention is shown which includes frame 1 having a distal cartridge member 2 connected to flexible hose containing gas conduit 3, liquid inlet 48, and liquid outlet 50 conduits. Frame 1 contains recess 104 for storage of the distal membrane unit cartridge 2; and includes power switch 52; liquid temperature gauge 40; external air intake filter 90 port; Vapotherm TM timer and switch 59; liquid heater power light 42; Vapotherm TM light 55; overtemp activity light 45 interacting with vapor/gas delivery tube 51; liquid ambient reservoir 31; vapor/gas exit use port; 27 and back pressure valve 29. Other operative elements of this apparatus (not shown) are described in FIGS. 1, 2, 6, and 9.

Figure 8:
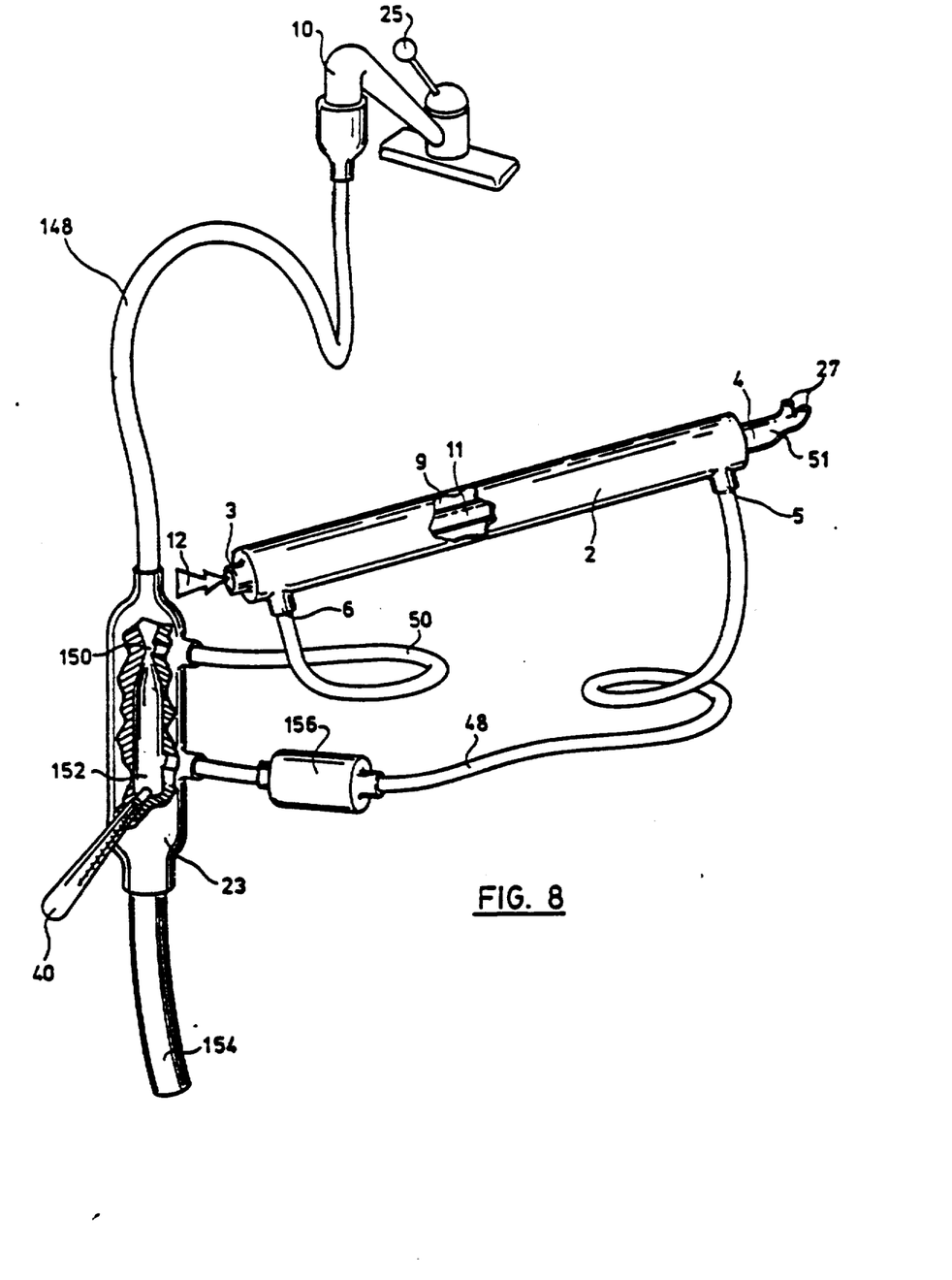
FIG. 8 is a front perspective view of another apparatus according to the invention.

Referring to FIG. 8 which is a view of another preferred embodiment of this invention, an apparatus is connected to a liquid supply source 10 having a manual liquid temperature regulator 25 which combines and/or regulates one or more liquid streams to the desired membrane container liquid inlet port 5 outlet port 6 temperature. In operation, the liquid flows through chamber 9 in contact with external hollow tube surface 11 under negative vacuum pressure provided and maintained by venturi vacuum pump 23 containing a reduced opening 150 which substantially uniformly diverges to an enlarged opening 152. Liquid passing through liquid source conduit 148 is connected to pump 23 and enters inlet conduit line 48 and exits liquid conduit line 50. Integral within membrane container 2 are inlet gas port 3 coaxially alligned with tube 13—which extends from port 3 through membrane container 2 to outlet gas port 4—coaxially alligned with disposable canula 51 containing nare prongs 27. Venturi pump housing contains thermometer 40.

Figure 9:
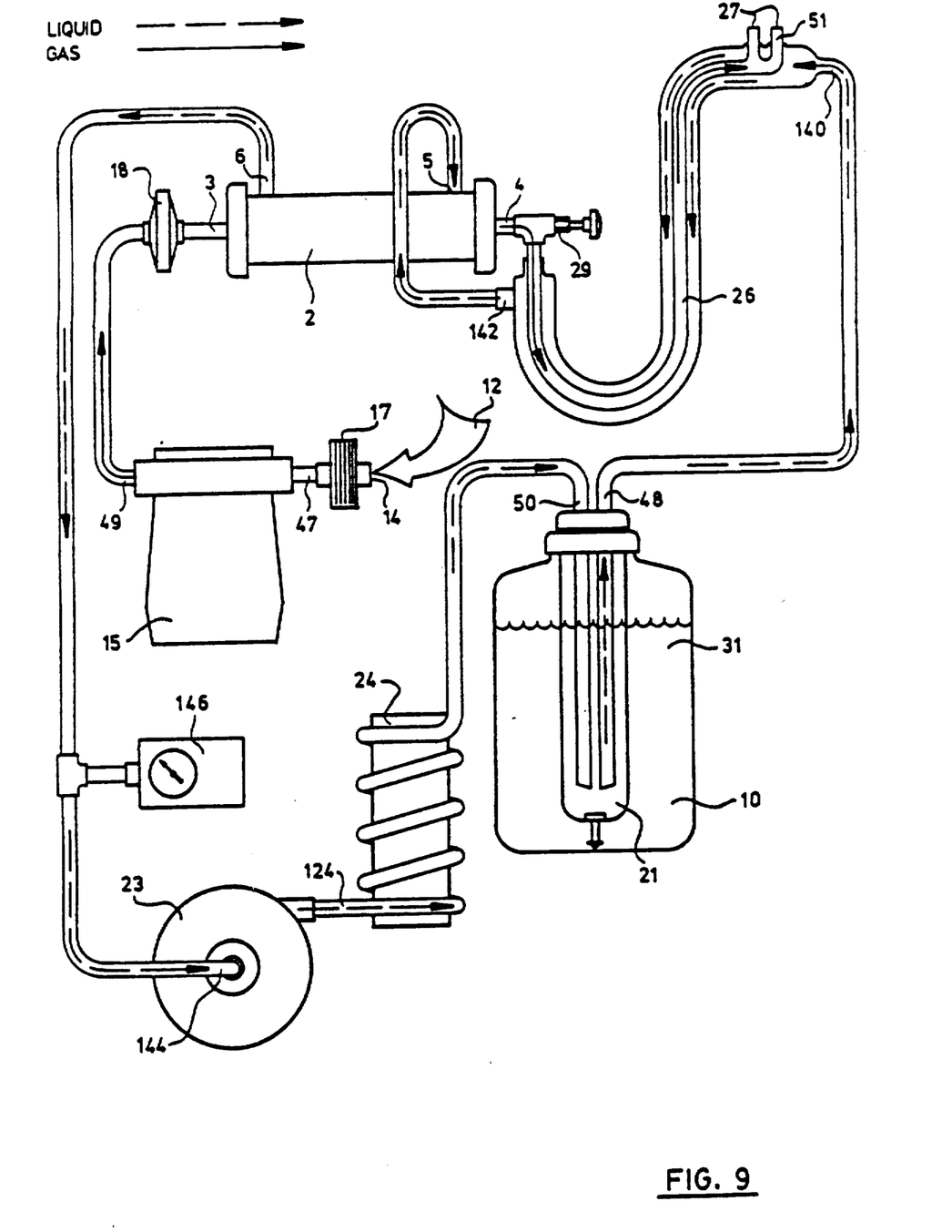
FIG. 9 is a schematic diagram of another preferred apparatus according to the invention.

Referring to FIG. 9, another schematic diagram illustrates another inventive embodiment including a membrane container 2 containing permeable membrane hollow fibers. In operation, liquid 10 is drawn from sequestered reservoir 21—maintained at the nare exit port 27 vapor/gas dew point delivery temperature by adjusting the temperature of liquid exiting vacuum pump 23 port 124 using heater 24. Sequentially, liquid enters port 140; passes through to heated delivery tube 26 flowing in a direction counter-current to gas flow exiting port 27; exits from port 142 into port 5, flows through liquid flow chamber external to the hollow fiber surfaces (all not shown); exits under negative vacuum pressure at membrane outlet port 6; and returns to vacuum pump 23. Sequentially, gas 12 enters port 14; passing through bacteria filter 17; into pump 15; through bacteria filter 18 and into membrane container at port 3. Gas passes through the internal membrane hollow fibers (not shown) and exits gas port 4 at pressures controlled by back pressure valve 29. The liquid content of the sequestered container 21 is replenished by room temperature or ambient temperature liquid 10 contained in reservoir 31.

Although the methods hereinafter describe the administration of gaseous water vapor at or near dew point temperatures to a respiratory tract areas without unnecessary heat or excessive condensation at high-flow-humidity rates preferably carried out by means of a heated delivery tube unheated nasal cannula headset—the apparatuses described herein in depth can also be used in conjunction with a face or tracheal mask, ventilator, hood, tent, or burn/wound dressing delivery systems.

The method of this invention—useful for respiratory tract and/or mucous membrane treatment—broadly comprises (a) the use of a heated delivery tube unheated nasal cannula for the delivery of a nasal cannula vapor/-gas stream to a nasal passageway at delivery rates in excess of 8 liters per minute at dew point temperatures equal to or less than dry bulb temperatures and (b) heating of a delivery tube vapor/gas stream to a temperature sufficiently greater than the cannula nare dew point use temperature in order to cause a readily observable cannula condensation film to form near the nare exit use ports which signals that the appropriate cannula delivery stream dew point-dry bulb temperature differential exists which insures that the dry bulb nare exit temperature is equal to or greater than the nare dew point use temperature.

Long term high-humidity heated delivery tube unheated nasal cannula deliveries of saturated-water-vapor/gas streams above 93—within a temperature range of 93 F. (33.9C.) to 99 degrees (33.9 to 37.2 degrees celsuis) farenheit at delivery rates in excess of 8 liters per minute are useful in the treatment of chronic obstructive lung disease, especially at flow rates within the range of about 10 to 60 liters per minute.

The method of this invention also includes the treatment of respiratory tracts above body alveolus temperatures—approximately 98.6 degrees farenheit (37 degrees celsius) for short term periods, commonly less than approximately one half hour at temperatures of 99 to 109 degrees farenheight (37.2 to 42.8 degrees celsius) or higher at high flow rates, e.g., flow rates in excess of 20 liters to 60 liters per minute. Treatments at elevated temperatures are reportedly an effective means of acquiring relief to acute coryza perennial allergic rhinitis.

In the practice of the method this invention described above any apparatus can be used to provide a substantially saturated-water-vapor/gas feedstock to the heated delivery tube unheated nasal cannula headset.

We claim:

1. A method useful for respiratory tract and/or mucous membrane treatment comprising:

(a) providing a permeable membrane comprised of a hydrophilic hollow fibers having diameters of less than 500 microns and a wall thickness of less than 25 microns, said membrane structured and adapted to permit a liquid-vapor boundary substrate to form adjacent to an opposing vapor-gas boundary;

(b) delivering a gas to said vapor-gas membrane boundary;

(c) delivering a liquid to said liquid-vapor membrane boundary substrate from a membrane location dispersed and spaced apart from said vapor -gas membrane boundary;

(d) delivering negative liquid pressure to said liquid-vapor membrane boundary;

(e) delivering positive gas pressure to said vapor-gas membrane boundary;

(f) regulating the temperature at said liquid-vapor membrane boundary substrate to form a humidified vapor-gas stream;

(g) delivering said humidified vapor/gas stream to a heated delivery tube connected to an unheated nasal cannula for the delivery of a nasal cannula vapor/gas stream to a nasal passageway at delivery rates in excess of 8 liter per minute at dew point temperatures equal to or less than dry bulb temperatures and (h) heating of said delivery tube vapor/gas stream to a temperature sufficiently greater than the cannula nare dew point use temperature, which is within the range of from about 99 to 109 degrees Fahrenheight, in order to cause a readily observable cannula condensation film to form near the nare exit use ports which signals that the appropriate cannula delivery stream dew point-dry bulb temperature differential exists which insures that the dry bulb nare exit temperature is equal to or greater than said nare dew point use temperature.

2. The method of claim 1 wherein said nare delivery rate is from about 10 to 60 liters per minute

* * * * *

UNITED STATES PATENT AND TRADEMARK OFFICE
CERTIFICATE OF CORRECTION

PATENT NO. : 4,773,410

DATED : Sep. 27, 1988

INVENTOR(S) : Richard H. Blackmer et al.

It is certified that error appears in the above-identified patent and that said Letters Patent is hereby corrected as shown below:

On the title page, in item [54] and in column 1, line 3, "TRACK" should be --TRACT--.

The title page showing the illustrative figure should be deleted to appear as per attached title page.

In the drawings, the sheets of drawing consisting of Figs. 1 - 6, should be deleted to be replaced with the sheets of drawings consisting of Figs. 1 - 9, as shown on the attached pages.

Signed and Sealed this

Sixteenth Day of October, 1990

Attest:

HARRY F. MANBECK, JR.

Attesting Officer

Commissioner of Patents and Trademarks

United States Patent [19]

Blackmer et al.

[11] Patent Number: 4,773,410
[45] Date of Patent: Sep. 27, 1988

[54] METHOD AND APPARATUS FOR THE TREATMENT OF THE RESPIRATORY TRACK WITH VAPOR-PHASE WATER

[75] Inventors: Richard H. Blackmer; Christopher C. Consaul, both of Scotia, N.Y.

[73] Assignee: Transpirator Technologies, Inc., Somerset, N.J.

[21] Appl. No.: 70,142

[22] Filed: Jun. 25, 1987

Related U.S. Application Data

[63] Continuation of Ser. No. 659,405, Oct. 9, 1984, abandoned.

[51] Int. Cl.⁴ .............................................. A61M 16/00
[52] U.S. Cl. ........................... 128/203.26; 128/203.27; 128/204.17; 128/204.13
[58] Field of Search ....................... 128/200.24, 203.12, 128/203.26, 203.27, 203.16, 203.17, 204.17, 207.18, 204.13

[56] References Cited

U.S. PATENT DOCUMENTS

| | | | |
|---|---|---|---|
| 2,868,199 | 1/1959 | Hudson | 128/207.18 |
| 3,972,321 | 8/1976 | Proctor | 128/207.18 |
| 4,060,576 | 11/1977 | Grant | 128/203.27 |
| 4,146,597 | 3/1979 | Eckstein et al. | 128/204.13 |
| 4,155,961 | 5/1979 | Behthin | 128/204.13 |
| 4,201,204 | 5/1980 | Rinne et al. | 128/203.27 |
| 4,355,636 | 10/1982 | Oetjen et al. | 128/204.17 |
| 4,369,777 | 1/1983 | Lwoff et al. | 128/204.17 |
| 4,381,267 | 4/1983 | Jackson | 128/204.13 |
| 4,401,114 | 8/1983 | Lwoff et al. | 128/204.17 |

Primary Examiner—Edward M. Coven
Assistant Examiner—K. M. Reiche
Attorney, Agent, or Firm—Kane, Dalsimer, Sullivan, Kurucz, Levy, Eisele and Richard

[57] ABSTRACT

A method and an apparatus are described which are useful for respiratory tract therapy. The method comprises contact of mucous membranes with vapor-phase water in the substantial absence of nucleating water-vapor condensation particulate, and includes the use of a heated delivery tube, unheated nasal cannula, for the delivery of a nasal cannula vapor/gas stream to a nasal passageway at delivery rates in excess of 8 liters per minute at dew point temperatures equal to or less than dry bulb temperatures and heating of a delivery tube vapor-gas stream to a temperature sufficiently greater than the canula nare dew point use temperature in order to cause a readily observable cannula condensation film to form near the exit use ports thereby signaling that the appropriate cannula delivery stream dew point-dry bulb temperature differential exists which insures that the dry bulb nare exit temperature is equal to or greater than the nare dew point use temperature.

2 Claims, Drawing Sheets